United States Patent
Miles et al.

(10) Patent No.: US 6,835,552 B2
(45) Date of Patent: *Dec. 28, 2004

(54) IMPEDANCE MEASUREMENTS FOR DETECTING PATHOGENS ATTACHED TO ANTIBODIES

(75) Inventors: Robin R. Miles, Danville, CA (US); Kodumudi S. Venkateswaran, Livermore, CA (US); Christopher K. Fuller, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/737,542

(22) Filed: Dec. 14, 2000

(65) Prior Publication Data

US 2002/0076690 A1 Jun. 20, 2002

(51) Int. Cl.$^7$ .................. G01N 33/53; G01N 33/543
(52) U.S. Cl. .............. 435/7.32; 435/4; 435/6; 435/7.1; 435/7.9; 435/7.92; 435/287.1; 435/287.2; 435/287.9; 435/288.5; 435/817; 436/149; 436/518; 436/524; 436/528; 436/532; 436/536; 436/823; 204/193; 204/228.1; 204/228.6; 204/229.8; 204/230.2; 204/298.03; 204/298.32
(58) Field of Search .............. 435/4, 6, 7.1, 7.32, 435/7.9, 7.92, 817, 287.1–214.2, 287.9, 188.5, 287.2, 287.3, 288.5, 288.7, 808; 436/514, 524, 528, 532, 536, 806, 149, 823, 151, 164, 169, 172, 518, 535, 547, 805, 406, 815, 824, 829; 204/193, 228.1, 228.6, 229.8, 230.2, 298.03, 298.32, 400, 403, 406, 407, 409–412, 422, 424, 426, 435; 422/55, 57, 58, 68.1, 76, 77, 82.01–82.09, 82.11, 90, 91, 98, 119, 939

(56) References Cited

U.S. PATENT DOCUMENTS

| | | | | | |
|---|---|---|---|---|---|
| 3,966,580 | A | * | 6/1976 | Janata et al. | 204/195 B |
| 4,072,576 | A | * | 2/1978 | Arwin et al. | 195/103.5 R |
| 4,920,047 | A | * | 4/1990 | Giaever et al. | 435/7 |
| 5,001,048 | A | * | 3/1991 | Taylor et al. | 435/4 |
| 5,108,576 | A | * | 4/1992 | Malmros et al. | 204/403 |
| 5,141,868 | A | * | 8/1992 | Shanks et al. | 435/288 |
| 5,149,629 | A | * | 9/1992 | Rishpon et al. | 435/7.9 |
| 5,194,133 | A | * | 3/1993 | Clark et al. | 204/299 R |
| 5,204,239 | A | * | 4/1993 | Gitler et al. | 435/7.1 |
| 5,234,566 | A | * | 8/1993 | Osman et al. | 204/403 |
| 5,328,847 | A | * | 7/1994 | Case et al. | 435/291 |
| 5,374,521 | A | * | 12/1994 | Kipling et al. | 435/6 |
| 5,494,831 | A | * | 2/1996 | Kindler | 436/525 |
| 5,567,301 | A | * | 10/1996 | Stetter et al. | 205/777.5 |
| 5,622,872 | A | * | 4/1997 | Ribi | 436/518 |
| 5,653,939 | A | * | 8/1997 | Hollis et al. | 422/50 |
| 5,846,744 | A | * | 12/1998 | Athey et al. | 435/7.9 |
| 5,942,388 | A | * | 8/1999 | Willner et al. | 435/6 |
| 6,074,827 | A | * | 6/2000 | Nelson et al. | 435/6 |
| 6,100,084 | A | * | 8/2000 | Miles et al. | 435/306.1 |
| 6,133,046 | A | * | 10/2000 | Clerc | 436/501 |
| 6,180,335 | B1 | * | 1/2001 | Wilkins et al. | 435/4 |
| 6,348,319 | B1 | * | 2/2002 | Braach-Maksvytis et al. | 204/400 |
| 6,358,752 | B1 | * | 3/2002 | Durst et al. | 204/194 |
| 6,383,354 | B1 | * | 5/2002 | Kurokawa et al. | 204/406 |
| 6,387,707 | B1 | * | 5/2002 | Seul et al. | 422/50 |
| 6,437,551 | B1 | * | 8/2002 | Krulevitch et al. | 324/71.1 |
| 6,440,662 | B1 | * | 8/2002 | Gerwen et al. | 435/6 |
| 6,544,478 | B1 | * | 4/2003 | Oyama et al. | 422/82.01 |
| 2002/0070114 | A1 | * | 6/2002 | Miles | 204/452 |
| 2002/0150886 | A1 | * | 10/2002 | Miles et al. | 435/5 |

FOREIGN PATENT DOCUMENTS

| | | | |
|---|---|---|---|
| EP | 0 213 825 A2 | * | 3/1987 |
| GB | 2 136 130 A | * | 9/1984 |
| GB | 2 210 462 A | * | 6/1989 |
| GB | 2 215 846 A | * | 9/1989 |
| WO | WO-97/21094 A1 | * | 6/1997 |
| WO | WO-98/19153 A1 | * | 5/1998 |
| WO | WO-00/72019 A2 | * | 11/2000 |

* cited by examiner

*Primary Examiner*—Christopher L. Chin
*Assistant Examiner*—Kartic Padmanabhan
(74) *Attorney, Agent, or Firm*—Eddie E. Scott; L. E. Carnahan; Alan H. Thompson

(57) ABSTRACT

The use of impedance measurements to detect the presence of pathogens attached to antibody-coated beads. In a fluidic device antibodies are immobilized on a surface of a patterned interdigitated electrode. Pathogens in a sample fluid streaming past the electrode attach to the immobilized antibodies, which produces a change in impedance between two adjacent electrodes, which impedance change is measured and used to detect the presence of a pathogen. To amplify the signal, beads coated with antibodies are introduced and the beads would stick to the pathogen causing a greater change in impedance between the two adjacent electrodes.

14 Claims, 3 Drawing Sheets

IMPEDANCE MEASUREMENTS FOR DETECTING PATHOGENS ATTACHED TO ANTIBODIES

The United States Government has rights in this invention pursuant to Contract No. W-7405-ENG-48 between the United States Department of Energy and the University of California for the operation of Lawrence Livermore National Laboratory.

BACKGROUND OF THE INVENTION

Field of the Invention

The present invention relates to detecting the presence of pathogens trapped in an electric field of a fluidic device, particularly to pathogens attached to antibodies immobilized in the electric field, and more particularly to the use of impedance measurements for detecting the presence of pathogens attached to antibody—coated beads located in the electric field.

Dielectrophoresis (DEP) is currently utilized to collect or concentrate pathogens in an electric field of a fluidic device. Recently, interdigitated electrodes have been patterned on the surface of a fluidic channel for generation of a non-uniform electric field by applying a voltage across the electrodes and pathogens are trapped by the dielectrophoretic force.

One typical method of detecting pathogens is to detect whether or not they attach to specific antibodies. The antibodies are typically fluorescently labeled and this increase in fluorescence is detected optically. Multiple pathogen detection has been accomplished by immobilizing antibodies on a surface, and then introducing pathogens in a fluid to the surface. The pathogen binds to the surface and then are detected by optical means.

Recently, impedance measurements across adjacent electrodes has been utilized to detect the presence of trapped pathogens, and such an approach has been described and claimed in co-pending application Ser. No. 09/738,927, filed Dec. 13, 2000, entitled "Using Impedance Measurements For Detecting Pathogens Trapped In An Electric Field", assigned to the same assignee.

The present invention expands the impedance measurement approach to detect the presence of pathogens attached to immobilized antibodies, and to the use of antibody-coated beads for enhancing the impedance change to amplify this impedance change signal. The present invention utilizes patterned interdigitated electrodes located on the surface of a fluidic channel with an AC or DC voltage is applied across the electrodes, antibodies are immobilized on the surface of the electrodes and pathogens flowing in a sample fluid therepast are attached to the immobilized antibodies causing a change in impedance between adjacent electrodes. This impedance change can be enhanced by providing antibody-coated beads that attach to the pathogens thereby causing a greater impedance change.

SUMMARY OF THE INVENTION

It is an object of the invention to detect pathogens attached antibodies in a fluidic flow channel.

A further object of the invention is to detect the attachment of pathogens to immobilized antibodies in an electric field by measuring impedance change between adjacent electrodes caused by the presence of the pathogens.

Another object of the invention is to detect the attachment of antibodies to pathogens using the change of impedance between two electrodes.

Another object of the invention is to provide a sensor to detect the presence of pathogens trapped in an electric field or attached to antibodies immobilized in the field by measurement of impedance changes between two patterned electrodes located in a fluidic channel.

Another object of the invention is to enhance an impedance change signal causes by pathogens being trapped in an electric field by providing antibody-coated beads that attach to the trapped pathogens causing a greater impedance change.

Another object of the invention is to detect pathogens trapped in an electric field by providing antibody coated beads which attach to the pathogens causing further change in the impedance between two electrodes, and moving the thus coated beads in an out of the signal region.

Another object of the invention is to provide a device for measuring impedance change in electrodes located in a fluidic channel and caused by trapped pathogens, and providing a second set of electrodes to act as a reference signal.

Other objects and advantages of the present invention will become apparent from the following description and accompanying drawings. The present invention is directed to the use of impedance measurements to detect the presence of pathogen attached to antibodies, and more particular to pathogens attached to antibody coated beads. Basically, the present invention replaces the prior optical detection approach with the detection of the attachment of antibodies to pathogens using the change of impedance between two electrodes as a way of making a less expensive pathogen detection system. The detection system or sensor of this invention, may for example, use patterned intedigitated electrodes on the surface of a fluid channel, with an AC or DC voltage applied across the electrodes to produce a non-uniform electric field. Antibodies are immobilized on the surfaces of the electrodes and the impedance between the electrodes is measured. Following the passage of a sample fluid containing pathogens through the fluid channel and by the electrode surface, certain of the pathogen are attached to the immobilized antibodies, thereby causing a change in the impedance between the electrodes, which change of impedance provides a measurement by which the presence of the pathogens can be determined. To amplify the impedance change signal, antibody coated bead may be introduced which attach to the trapped pathogens causing a greater change in impedance between the electrodes. The pathogen sensor of this invention can be used, for example, in counter biological warfare detectors to detect the presence of pathogens, or in any antibody-based assay system.

BRIEF DESCRIPTION OF THE DRAWINGS

The accompanying drawings, which are incorporated into a form a part of the disclosure, illustrate embodiments of the invention and, together with the description, serve to explain the principles of the invention.

DETAILED DESCRIPTION OF THE INVENTION

The present invention is directed to a method and apparatus (sensor) for detecting the presence of pathogens attached to antibodies, either immobilized or coated on beads, by the use of impedance measurements between electrodes. The invention can be utilized, for example, for detecting pathogens to determine whether or not the pathogens attached to specific antibodies, or merely to detect the presence of pathogens in a sample fluid flowing past immobilized antibodies. By the detection of the attachment of antibodies to pathogens using the change of impedance between two electrodes, or two adjacent legs of two multileg interdigitated electrodes, a less expensive pathogen detection system is provided compared to the previously utilized optical detection system, due to the reduction in instrumental costs.

Figure 2:
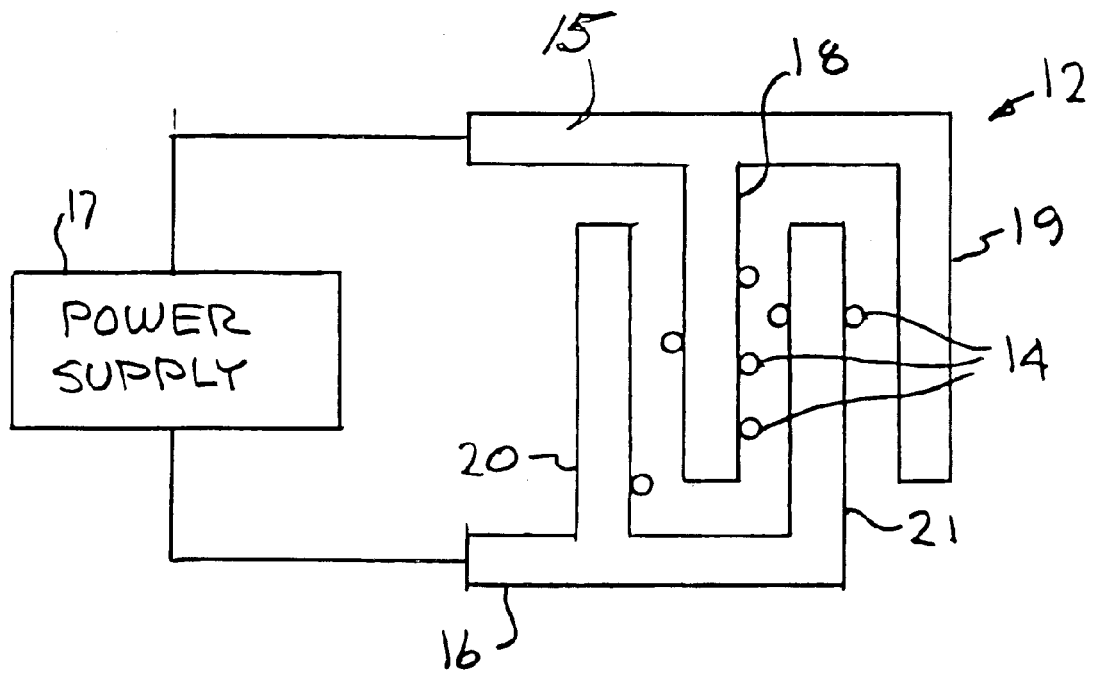
FIG. 2 is an enlarged to view of the patterned interdigitated electrodes of FIG. 1 with an AC power supply connected across the two electrodes to produce the electric field illustrated in FIG. 1.
Figure 3:
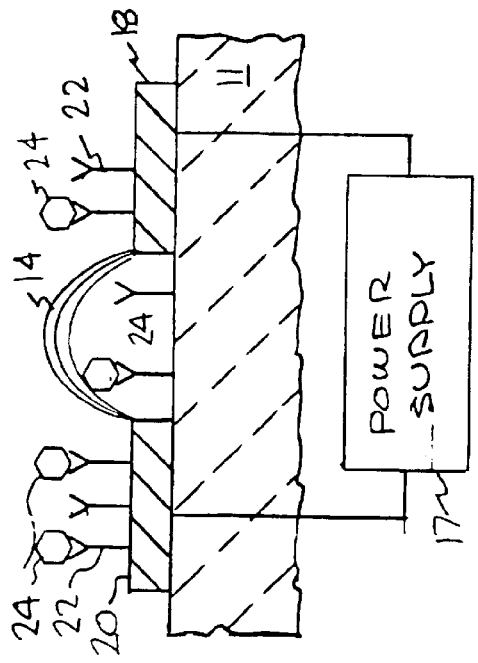
FIG. 3 illustrates only a pair of the electrode legs of FIGS. 1 and 2 for simplicity with antibodies immobilized on the surfaces of the electrodes in accordance with the present invention.
Figure 4:
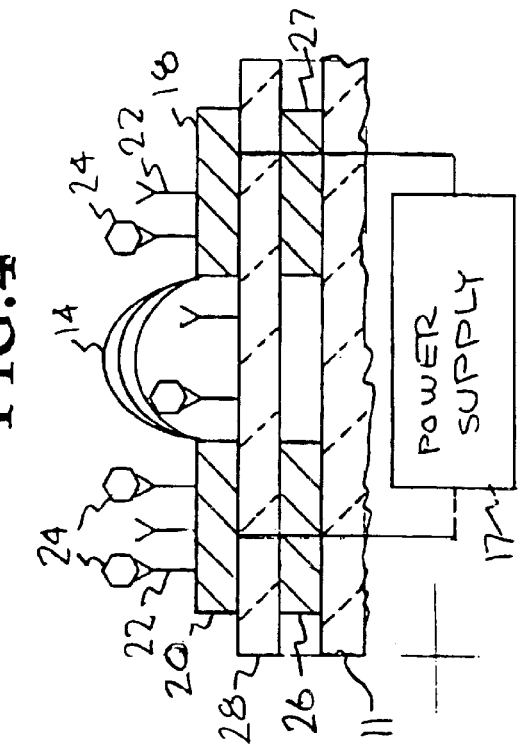
FIG. 4 illustrates the electrodes of FIG. 3 with pathogens attached to certain of the immobilized antibodies.
Figure 5:
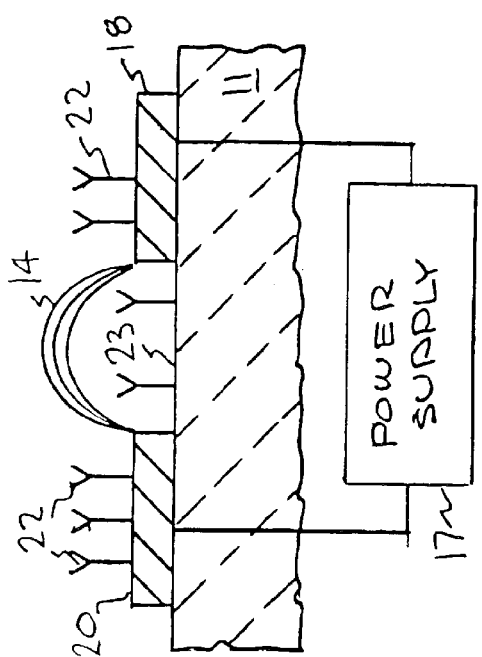
FIG. 5, which is similar to FIG. 4, additionally illustrates the addition of antibody-coated beads which attach to the pathogens for amplifying the impedance change between the electrodes.
Figure 6:
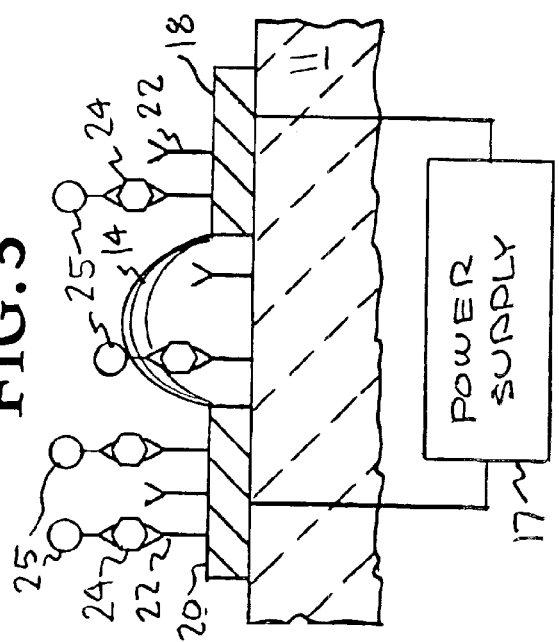
FIG. 6 illustrates an embodiment of an arrangement similar to FIG. 4, but with the addition of a pair of reference electrodes spaced via an insulator from the two electrodes of FIG. 4.
Figure 7:
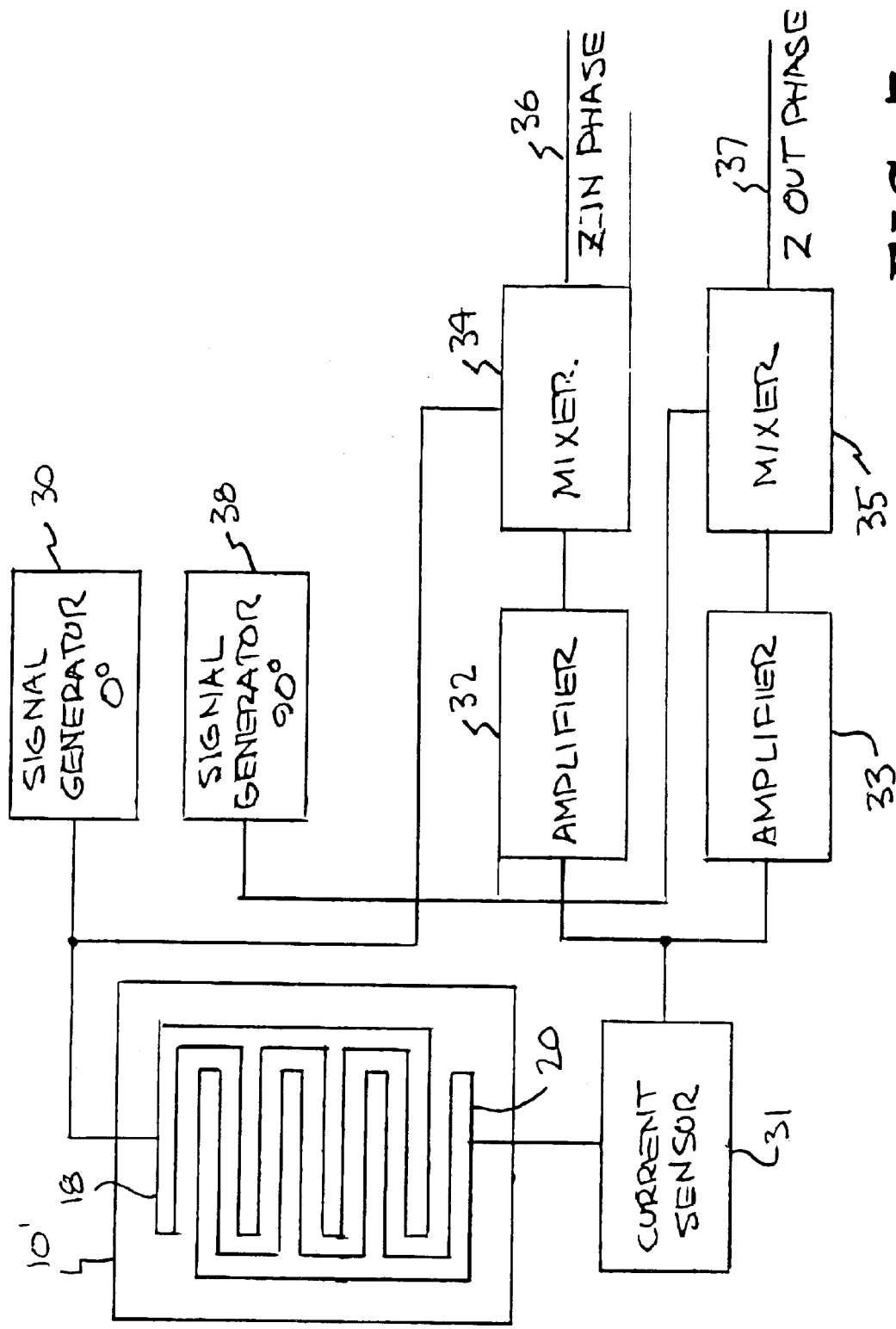
FIG. 7 schematically illustrates an impedance sensor mounted to the two electrodes of FIGS. 3–5.

Since antibodies can be immobilized on a surface, the present invention utilizes surfaces of two spaced electrodes or two adjacent legs of patterned interdigitated electrodes as a surface on which the antibodies are immobilized, as illustrated in FIG. 3 and described in detail hereinafter, the electrodes of FIG. 3 being two of the adjacent legs of the interdigitated electrodes of FIGS. 1 and 2. The pathogen streaming by the electrode surfaces attach to the immobilized antibodies, as seen in FIG. 4, and thus changes the impedance between the two electrodes, which is measured, as by the sensor of FIG. 7, to detect the presence of a pathogen. To amplify this impedance change signal, one or more beads coated with antibodies are introduced into the sample fluid flow, and the beads stick to the trapped pathogen as seen in FIG. 5. The coated beads further add to the change in impedance between the two electrodes. The coated bead or beads can be moved in and out of the signal region using either electrophoretic, dielectrophoretic, magnetic, or pressure flow modes so that the bead or beads could be recycled. Beads bound to pathogen could be eluted and the surface reactivated. Also, a second set of electrodes could be placed beneath the first set to act as a reference signal, as shown in FIG. 6. The sensor of FIG. 7 is shown operatively connected to two electrodes, such as shown in FIGS. 3–6, but may be expanded to be connected between two adjacent legs of the interdigitated electrodes of FIG. 2.

Figure 1:
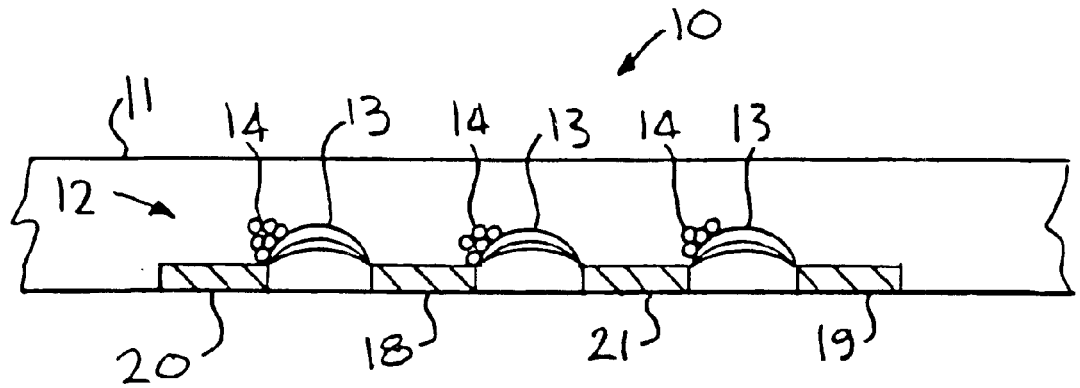
FIG. 1 illustrates in cross-section a fluidic channel with patterned interdigitated electrodes formed on a surface of the channel with electrode fields shown across the various legs of the interdigitated electrodes.

Referring now to the drawings, FIG. 1 illustrates a cross-section of a fluidic channel with patterned interdigitated electrodes located on a surface of the channel, and with FIG. 2 illustrating a top view of the interdigitated electrodes of FIG. 1. As shown, a fluid device 10 includes at least one fluidic channel or microchannel 11 having patterned on an interior surface thereof a pair of interdigitated electrodes indicated generally at 12 and 13, across each adjacent leg pair is formed an electric field 14. As seen in FIG. 2, each electrode 12 and 13 includes a base section or member 15 and 16 to which an AC power supply 17 is connected to produce the electric fields 14 of FIG. 1. The power supply 17 may be of a DC type. Extending from each of the base members 15 and 16 of electrodes 12 and 13 are a pair of fingers or members 18–19 and 20–21, respectively, with finger 18 located intermediate fingers 20 and 21, with finger 21 located intermediate fingers 18 and 19. Thus, each adjacent pair of fingers (20–18, 18–21, and 21–19) form a pair of spaced electrodes across which an electric field 14 is created by applied voltage from AC power supply 17. The electrodes can be located within the fluidic channel by use of spaced wires or suspended structures.

In the embodiments illustrated in FIGS. 3–5 and FIG. 6, only two electrodes are shown for simplicity of illustration, and such are illustrated as electrodes or electrode fingers 20 and 18 of FIGS. 1 and 2. In FIGS. 3–6, components corresponding to components of FIGS. 1 and 2 are given corresponding reference numeral. The electrodes can be straight, as shown, or can be curved, with either uniform or variable widths or thickness.

As shown in FIG. 3, antibodies 22 are immobilized on the surface of electrodes 20 and 18 and the exposed surface 23 of channel 11 between the electrodes. As sample fluid streams pass the immobilized antibodies 22 on electrodes 20 and 18, pathogens in the sample fluid attach to the immobilized antibodies 22 as shown by pathogen 24 in FIG. 4. An impedance measurement between electrodes 20 and 18 is made prior to the passage of the sample fluid across the electrodes and after passage of the sample fluid, and the change in the impedance caused by the trapped pathogen is determined and measured to detect the presence of the pathogen by the impedance sensor of FIG. 7.

To amplify the impedance change signal, one or more beads 25 coated with antibodies can be introduced to the signal area (electrodes 20–18) as shown in FIG. 5. The coated bead or beads 25 stick to the pathogen 24 and further add to the change in impedance between the electrodes 20 and 18. As pointed out above the bead or beads 25 can be moved in and out of the signal region using either electrophoretic, dielectrophoretic, magnetic, or pressure flow mode, known in the art, so that the beads could be recycled. Also, the beads 25 could be eluted and the surface reactivated.

As shown in FIG. 6, a pair of electrodes 26 and 27, electrically connected to power supply 17 are located beneath the electrodes 20 and 18 to act as a reference signal. The reference electrodes 26 and 27, in the FIG. 6 embodiment are separated from electrodes 20 and 18 by a thin (~1 $\mu$m) insulator layer 28. If reference electrodes, as in FIG. 6 is utilized with interdigitated electrodes 12 and 13 of FIGS. 1 and 2, a reference electrode would be located beneath each of the electrode legs 18–21.

FIG. 7, illustrates an embodiment of an impedance sensor, which as illustrated is operatively connected only to electrodes 20 and 18 for simplicity of illustration. It is to be recognized that the sensor embodiment of FIG. 7 would need be modified to sense each adjacent pair of the interdigitated electrode legs 18–21 of FIGS. 1 and 2, and such modification is within the skill of the art.

As shown in FIG. 7, this embodiment comprises electrodes 18 and 20 located in a microchannel device 10', with a 0° signal generator 30 electrically connected to electrode 18 and a current sensor 31 electrically connected to electrode 20. A pair of amplifiers 32 and 33 are connected in parallel to current sensor 31, with mixers 34 and 35 operatively connected to amplifiers 32 and 33, which measure the impedance (z) in-phase, indicated at 36, and out-of-phase indicated at 37, of the components of the device. A 90° signal generator 38 is electrically connected to the mixer 35, with signal generator 30 electrically connected to mixer 34. Signal generators 30 and 38 drive dielectrophoretic device electrodes 18 and 20. Collected particles cause a change in the device impedance, as described above, and the output of the current sensor 31. Amplifiers 32 and 33 and mixers 34 and 35 measure the in-phase 36 and out-of-phase 37 components of the devices complex impedance.

It has thus been shown that the present invention enables the use of impedance measurements to detect the presence of pathogens attached to immobilized antibodies and/or beads coated with antibodies. The impedance change pathogen detection approach of the present invention provides a simplified and less expensive system than the prior utilized optical detection systems. The sensor of this invention can be effectively utilized in antibody-based assay system as well as for detecting the presents of pathogens in counter biological warfare detectors.

While particular embodiments of the present invention have been illustrated and described to exemplify and teach the principles of the invention. Modifications and changes may become apparent to those skilled in the art, and it is intended that the invention be limited only by the scope of the appended claims.

What is claimed is:

1. An apparatus for determining trapping of pathogens carried by a fluid by antibodies deposited in a fluidic channel, comprising:

a fluidic channel having at least one pair of spaced electrodes having surfaces and with a space between said electrodes, said electrodes localized along a length of said fluidic channel, with the electrodes of said at least one pair being located on the same side of said fluidic channel, antibodies immobilized on said surfaces of said spaced electrodes and immobilized in said space between said electrodes wherein said pathogens carried by said fluid attach to said immobilized antibodies, beads coated with antibodies located in said space between said electrodes wherein said beads coated with antibodies stick to the pathogens, means for producing an electric field across said spaced electrodes, and an impedance sensor for measuring impedance between said spaced electrodes for determining trapping of said pathogens by measuring change in impedance between said pair of spaced electrodes with said beads coated with antibodies amplifying the change in impedance.

2. The apparatus of claim 1, additionally including at least one pair of reference electrodes located in spaced relation to said at least one pair of spaced electrodes, an insulator located between said reference electrodes and said pair of spaced electrodes, said reference electrodes being electrically connected to said impedance sensor.

3. The apparatus of claim 1, wherein said at least one pair of spaced electrodes is located on a surface of said fluidic channel.

4. The apparatus of claim 3, wherein said at least one pair of spaced electrodes comprises a plurality of adjacent pairs of spaced electrodes.

5. The apparatus of claim 4, wherein said plurality of adjacent pairs of spaced electrodes are formed by adjacent fingers of an interdigitated electrode located on the surface of said fluidic channel.

6. The apparatus of claim 1, wherein said means for producing an electric field across said spaced electrodes comprises an AC power supply.

7. A sensor using impedance measurements to detect the presence of pathogens attached to antibodies wherein said pathogens are carried by a fluid, comprising:

a microfluidic device having at least one microchannel therein, at least one pair of spaced electrodes located on a surface along a length of said microchannel, said pair of spaced electrodes having surfaces and being located on the same surface of the microchannel with a space between said electrodes, antibodies immobilized on said surfaces of said spaced electrodes and immobilized in said space between said electrodes wherein said pathogens carried by said fluid attach to said immobilized antibodies, beads coated with antibodies located in said space between said electrodes wherein said beads coated with antibodies stick to the pathogens, an AC or DC power supply for producing an electric field across said spaced electrodes, and means for measuring impedance between said spaced electrodes to detect the presence of said pathogens by measuring change in impedance between said pair of spaced electrodes with said beads coated with antibodies amplifying the change in impedance.

8. The sensor of claim 7, wherein said spaced electrodes comprise fingers of an interdigitated electrode formed on said surface of said microchannel.

9. The sensor of claim 8, wherein said interdigitated electrode includes fingers forming a plurality of adjacent pairs of spaced electrodes.

10. The sensor of claim 6, additionally including reference electrodes located in insulated relation to said spaced electrodes and electrically connected to said means for measuring impedance.

11. The sensor of claim 7, wherein said means for measuring impedance between said spaced electrodes includes a plurality of signal generators, a current sensor connected to at least one electrode, a plurality of amplifier/mixer assemblies connected in parallel to said current sensor, said signal generators each being connected to one of said amplifier/mixer assemblies, and one of said signal generators being additionally connected to another of said spaced electrodes.

12. The sensor of claim 7, wherein the at least one pair of spaced electrodes is formed within the fluidic channel.

13. The apparatus of claim 7, wherein said spaced electrodes are located in a bottom surface of said fluidic channel.

14. The sensor of claim 7, wherein said spaced electrodes are located in a bottom surface of said at least one microchannel.

* * * * *